United States Patent
Bund et al.

(10) Patent No.: US 12,252,519 B2
(45) Date of Patent: Mar. 18, 2025

(54) CRYSTAL STRUCTURE OF A REPLICATION PROTEIN ENCODED BY A PLASMID ISOLATED FROM A MULTIPLE SCLEROSIS PATIENT

(71) Applicant: DEUTSCHES KREBSFORSCHUNGSZENTRUM STIFTUNG DES ÖFFENTLICHEN RECHTS, Heidelberg (DE)

(72) Inventors: Timo Bund, Dossenheim (DE); Grant S. Hansman, Heidelberg (DE); Turgay Kilic, Heidelberg (DE); Alexander N. Popov, Grenoble (FR); Ethel-Michele De Villiers-Zur Hausen, Waldmichelbach (DE); Harald Zur Hausen, Waldmichelbach (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 941 days.

(21) Appl. No.: 17/242,116

(22) Filed: Apr. 27, 2021

(65) Prior Publication Data
US 2021/0246178 A1  Aug. 12, 2021

Related U.S. Application Data

(63) Continuation of application No. PCT/EP2019/081364, filed on Nov. 14, 2019.

(30) Foreign Application Priority Data

Nov. 15, 2018 (EP) .................................. 18206532

(51) Int. Cl.
C07K 14/47 (2006.01)
G01N 33/68 (2006.01)
G16B 35/20 (2019.01)

(52) U.S. Cl.
CPC ..... *C07K 14/4703* (2013.01); *G01N 33/6893* (2013.01); *G16B 35/20* (2019.02); *C07K 2299/00* (2013.01)

(58) Field of Classification Search
CPC ............ C07K 14/4703; C07K 2299/00; G16B 35/20; G01N 33/6893
See application file for complete search history.

(56) References Cited

PUBLICATIONS

McPherson, A., "Current approaches to macromolecular crystallization." Eur. J. Biochem. 189, 1-23. (Year: 1990).*
Kundrot et al. "Which strategy for a protein crystallization project?" Cell. Mol. Life Sci., 61: 525-536 (Year: 2004).*
Benvenuti and Mangani "Crystallization of proteins in vapor diffusion for x-ray crystallography." Nat Protoc 2, 1633-1651. (Year: 2007).*
Moon et al., "A synergistic approach to protein crystallization: Combination of a fixed-arm carrier with surface entropy reduction." Protein Science, 19:901-913 (Year: 2010).*
R. Cudney, "Protein Crystallization and Dumb Luck" Rigaku Journal, vol. 16, No. 1, pp. 1-7 (Year: 1999).*
Drenth, "Principles of Protein X-Ray Crystallography", 2nd Edition, Springer-Verlag New York Inc., Chapter 1, p. 19, 4th paragraph, lines 1-2 (Year: 1999).*
McPherson and Gavira, "Introduction to protein crystallization." Structural Biology Communications. Acta Cryst. F70, 2-20 (Year: 2014).*
Eilebrecht, S. et al. "Expression and replication of virus-like circular DNA in human cells" Scientific Reports, 2018, vol. 8, No. 1, 15 pages.
EMBL Database, "Sphinx1.76-related DNA replication protein", XP002790160, retrieved from EBI accession No. EMBL: CDS63398. Abstract. 1 page.
Falida, K. et al. "Isolation of Two Virus-Like Circular DNAs from Commercially Available Milk Samples" Genome Announcements, 2017, vol. 5, No. 17, 2 pages.
Funk, M. et al. "Isolation of Protein-Associated Circular DNA from Healthy Cattle Serum" Genome Announcements, 2014, vol. 2, No. 4, 2 pages.
Giraldo, R. et al. "A conformational switch between transcriptional repression and replication initiation in the RepA dimerization domain" Nature Structural Biology, 2003, vol. 10, No. 7, pp. 565-571.
Giraldo, R. et al. "RepA-WH1 prionoid: Clues from bacteria on factors governing phase transitions in amyloidogenesis" Prion, 2016, vol. 10, pp. 41-49.
Gunst, K. et al. "Isolation of Bacterial Plasmid-Related Replication-Associated Circular DNA from a Serum Sample of a Multiple Sclerosis Patient" Genome Announcements, 2014, vol. 2, No. 4. 1 page.
International Search Report for PCT Application No. PCT/EP2019/081364. Mail Date: May 7, 2020. 6 pages.
Komori, H. et al. "Crystallization and preliminary X-ray diffraction studies of a replication initiator protein (RepE54) of the mini-F plasmid complexed with iteron DNA" J. Biochem., 1999, vol. 125, pp. 24-26.
Nakamura, A. et al. "Expression and purification of F-plasmid RepE and preliminary X-ray crystallographic study of its complex with operator DNA" Acta Crystallographics, 2007, F63, pp. 346-349.
Swan, M. et al. "Crystal structure of π initiator protein-iteron complex of plasmid R6K: Implications for initiation of plasmid DNA replication" PNAS, 2006, vol. 103, No. 49, pp. 18481-18486.
Whitley, C. et al. "Novel Replication-Competent Circular DNA Molecules from Healthy Cattle Serum and Milk and Multiple Sclerosis-Affected Human Brain Tissue" Genome Announcements, 2014, vol. 2, No. 4. 2 pages.

(Continued)

*Primary Examiner* — Suzanne M Noakes
*Assistant Examiner* — Ciara A McKnight
(74) *Attorney, Agent, or Firm* — Perkins Coie LLP; Viola Kung (57) ABSTRACT

The present invention relates to crystal forms of a replication protein encoded by a plasmid isolated from a Multiple Sclerosis patient, crystal structure information obtained from them, methods of preparing such crystal forms, their use for the identification and/or design of inhibitors of said replication proteins and methods for identifying, optimizing and designing compounds which should have the ability to interact with or inhibit the replication protein.

6 Claims, 5 Drawing Sheets

Specification includes a Sequence Listing.

(56) References Cited

PUBLICATIONS

Yan, S. et al. "Thiazolone-acylsulfonamides as novel HCV NS5B polymerase allosteric inhibitors: Convergence of structure-based drug design and X-ray crystallographic study" Bioorganic & medicinal Chemistry Letters, 2007, vol. 17, pp. 1991-1995.

Chayen, N. et al. "Protein crystallization: from purified protein to diffraction-quality crystal" Nature Methods, 2008, vol. 5, pp. 147-153. Abstract Only. 1 page.

* cited by examiner

SEQUENCE LISTING

<160> NUMBER OF SEQ ID NOS: 2

<210> SEQ ID NO 1
<211> LENGTH: 324
<212> TYPE: PRT
<213> ORGANISM: Sphinx
<220> FEATURE:
<223> OTHER INFORMATION: MSBI1.76 protein

<400> SEQUENCE: 1

Met Ser Asp Leu Ile Val Lys Asp Asn Ala Leu Met Asn Ala Ser Tyr
1               5                   10                  15

Asn Leu Ala Leu Val Glu Gln Arg Leu Ile Leu Ala Ile Ile Glu
            20                  25                  30

Ala Arg Glu Thr Gly Lys Gly Ile Asn Ala Asn Asp Pro Leu Thr Val
            35                  40                  45

His Ala Ser Ser Tyr Ile Asn Gln Phe Asn Val Glu Arg His Thr Ala
        50                  55                  60

Tyr Gln Ala Leu Lys Asp Ala Cys Lys Asp Leu Phe Ala Arg Gln Phe
65                  70                  75                  80

Ser Tyr Gln Glu Lys Arg Glu Arg Gly Arg Ile Asn Ile Thr Ser Arg
                85                  90                  95

Trp Val Ser Gln Ile Gly Tyr Met Asp Asp Thr Ala Thr Val Glu Ile
                100                 105                 110

Ile Phe Ala Pro Ala Val Val Pro Leu Ile Thr Arg Leu Glu Glu Gln
            115                 120                 125

Phe Thr Gln Tyr Asp Ile Glu Gln Ile Ser Gly Leu Ser Ser Ala Tyr
130                 135                 140

Ala Val Arg Met Tyr Glu Leu Leu Ile Cys Trp Arg Ser Thr Gly Lys
145                 150                 155                 160

Thr Pro Ile Ile Glu Leu Asp Glu Phe Arg Lys Arg Ile Gly Val Leu
                165                 170                 175

Asp Thr Glu Tyr Thr Arg Thr Asp Asn Leu Lys Met Arg Val Ile Glu
            180                 185                 190

Leu Ala Leu Lys Gln Ile Asn Glu His Thr Asp Ile Thr Ala Ser Tyr
        195                 200                 205

Glu Gln His Lys Lys Gly Arg Val Ile Thr Gly Phe Ser Phe Lys Phe
    210                 215                 220

Lys His Lys Lys Gln Asn Ser Asp Lys Thr Pro Lys Asn Ser Asp Ser
225                 230                 235                 240

Ser Pro Arg Ile Val Lys His Ser Gln Ile Pro Thr Asn Ile Val Lys
                245                 250                 255

Gln Pro Glu Asn Ala Lys Met Ser Asp Leu Glu His Arg Ala Ser Arg
            260                 265                 270

Val Thr Gly Glu Ile Met Arg Asn Arg Leu Ser Asp Arg Phe Lys Gln
        275                 280                 285

Gly Asp Glu Ser Ala Ile Asp Met Met Lys Arg Ile Gln Ser Glu Ile
    290                 295                 300

Ile Thr Asp Ala Ile Ala Asp Gln Trp Glu Ser Lys Leu Glu Glu Phe
305                 310                 315                 320

Gly Val Val Phe

<210> SEQ ID NO 2
<211> LENGTH: 131
<212> TYPE: PRT
<213> ORGANISM: Sphinx

```
<220> FEATURE:
<223> OTHER INFORMATION: RepA domain

<400> SEQUENCE: 2

Met Val Asp Asn Lys Val Thr Gln Ser Asn Lys Leu Ile Glu Ser Ser
1               5                   10                  15

His Thr Leu Thr Leu Asn Glu Lys Arg Leu Val Leu Cys Ala Ala Ser
                20                  25                  30

Leu Ile Asp Ser Arg Lys Pro Leu Pro Lys Asp Gly Tyr Leu Thr Ile
            35                  40                  45

Arg Ala Asp Thr Phe Ala Glu Val Phe Gly Ile Asp Val Lys His Ala
        50                  55                  60

Tyr Ala Ala Leu Asp Asp Ala Ala Thr Lys Leu Phe Asn Arg Asp Ile
65                  70                  75                  80

Arg Arg Tyr Val Lys Gly Lys Val Val Glu Arg Met Arg Trp Val Phe
                85                  90                  95

His Val Lys Tyr Arg Glu Gly Gly Cys Val Glu Leu Gly Phe Ser Pro
                100                 105                 110

Thr Ile Ile Pro His Leu Thr Met Leu His Lys Glu Phe Thr Ser Tyr
            115                 120                 125

Gln Leu Lys
130
```

CRYSTAL STRUCTURE OF A REPLICATION PROTEIN ENCODED BY A PLASMID ISOLATED FROM A MULTIPLE SCLEROSIS PATIENT

This application is a continuation of PCT/EP2019/081364, filed Nov. 14, 2019; which claims priority to EP Application No. 18206532.6, filed Nov. 15, 2018. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Apr. 21, 2021, and a size of 4.18 kilobytes. The Sequence Listing filed via EFS-Web is part of the specification and is hereby incorporated in its entirety by reference herein.

FIELD OF THE INVENTION

The present invention relates to crystal forms of a replication protein encoded by a plasmid isolated from a Multiple Sclerosis patient, crystal structure information obtained from them, methods of preparing such crystal forms, their use for the identification and/or design of inhibitors of said replication proteins and methods for identifying, optimizing and designing compounds which should have the ability to interact with or inhibit the replication protein.

BACKGROUND OF THE INVENTION

The consumption of bovine meat and milk are considered one kind of risk factor for the development of human degenerative and malignant diseases, e.g. colon and breast cancers (1-3). Indeed, epidemiologic data suggest there is a correlation of these cancers with the consumption of bovine products from Eurasian Aurochs-derived cattle (4-7). Bovine Meat and Milk Factors (BMMFs) are circular, single stranded episomal DNAs (<3 kb) that have been detected in bovine meat and milk products. BMMFs are thought to have roles in human malignant and degenerative diseases. BMMFs encode a replication initiator protein (Rep) that is actively transcribed and translated in human cells. Thus, BMMFs might represent a possible etiological agent of such diseases (0.8-10). However, BMMFs were also isolated from patients with multiple sclerosis and studies suggested these to be a possible infectious agent of this disease (10-13).

Typically, BMMFs encode an autonomous plasmid trans-acting replication initiator protein termed "Rep". The Rep binds at an origin of replication on the DNA (termed ori) and in most cases, comprises of a set of repetitive DNA elements (termed iterons), which are present within most BMMFs (5). Replication of various plasmids, including Circular Rep-Encoding Single-Stranded (CRESS) DNA viruses, also requires the binding of the Rep to a specific DNA sequence (14). Within prokaryotes, the Rep plays a central role in maintaining the plasmid copy number, as reported for the F plasmid in *Escherichia coli* (15). This regulation is also critical for the replication of plasmid-derived, bacterio-phage-like, or virus-like DNA genomes (16). Reps are essential for the replication of multidrug-resistant bacteria in humans (17) and studies have suggested that Reps have a role in transmissible amyloid proteinopathy (18-20).

The X-ray crystal structures of Reps have been well documented and the structural basis for autonomous replication has been described (24-27). The Reps are composed of two winged-helix domains (termed WH1 and WH2) that are essentially a fused N- and C-terminal protein. The Reps transform between monomeric and dimeric forms, depending on the specific function and binding to DNA (28). Large structural changes involving both domains complement these oligomeric forms. The structural transformation requires certain α-helix and β-strands on the Rep to be refolded and/or shifted (26). In the dimeric form, the Rep functions as a repressor, where the WH2 binds to each operator DNA repeat and the WH1 functions to form the dimerization interface. In the monomeric form, the Rep functions as replication initiators, where the WH1 undergoes a large structural movement, i.e. dimer dissociation, thereby allowing the WH1 to bind to the iteron end, while the WH2 binds to the opposite iteron end.

Recently, an episomal circular DNA (isolate MSBI1.176, accession LK931491.1) was isolated from a brain sample of a patient with multiple sclerosis (11). The MSBI1.176 Rep exhibits a 98% amino acid identity with the Sphinx-1.76 encoded Reps (GenBank ADR65123.1 and HQ444404.1), which were isolated from culture and brain preparations of transmissible encephalopathy-related agents (21). Moreover, there were indications for detection of Sphinx.1.76 encoded Reps in neural cells (GT1-cell line) and brain samples of mouse CNS, hamster CNS, and human glioblastoma based on Sphinx-1.76-specific antibodies (22). Serology based on the MSBI1.176 Rep antigen showed positive immune responses for healthy human blood donors and indicated a possibly pre-exposure towards these agents (23). Therefore, deciphering the functions of BMMFs in human malignant and degenerative disease is becoming increasingly important.

Object of the Present Invention

For deciphering the functions of BMMFs in human malignant and degenerative diseases it would be very helpful to have a crystal structure of MSBI1.176 Rep protein which, however, failed until now. Such a crystal structure would be also helpful for the identification and/or design of inhibitors of said replication proteins and methods for identifying, optimizing and designing compounds which should have the ability to interact with or inhibit the replication protein.

Thus, it is the objective of the present invention to provide crystal structure coordinates of MSBI1.176 Rep protein, methods to obtain the crystal form of MSBI1.176 Rep protein as well as methods for designing, identifying and optimizing compounds as inhibitors of MSBI1.176 Rep protein based on the crystal structure and crystal structure coordinates.

DETAILED DESCRIPTION OF THE INVENTION

The objective of the present invention is solved by the teachings of the independent claims. Further advantageous features, aspects and details of the invention are evident from the dependent claims, the description, the figures, and the examples of the present application.

Thus, the present invention concerns a crystal form of MSBI1.176 Rep protein as characterized in claim 1. Preferred embodiments are the subject-matter of the dependent claims.

MSBI1 Rep Original Full Length Replication Protein
GenBank: CDS63398.1
(Encoded in Replication Competent Episomal DNA MSBI1.176)
Embl accession DNA sequence: LK931491.1
source: multiple sclerosis-affected human brain
MSBI1.176 Putative Replication Intiator Protein (SEQ ID NO: 1)
MSDLIVKDNALMNASYNLALVEQRLILLAIIEARETGKGINANDPLTVH

ASSYINQFNVERHTAYQALKDACKDLFARQFSYQEKRERGRINITSRWV

SQIGYMDDTATVEIIFAPAVVPLITRLEEQFTQYDIEQISGLSSAYAVR

MYELLICWRSTGKTPIIELDEFRKRIGVLDTEYTRTDNLKMRVIELALK

QINEHTDITASYEQHKKGRVITGFSFKFKHKKQNSDKTPKNSDSSPRIV

KHSQIPTNIVKQPENAKMSDLEHRASRVTGEIMRNRLSDRFKQGDESAI

DMMKRIQSEIITDAIADQWESKLEEFGVVF

Figure 1:
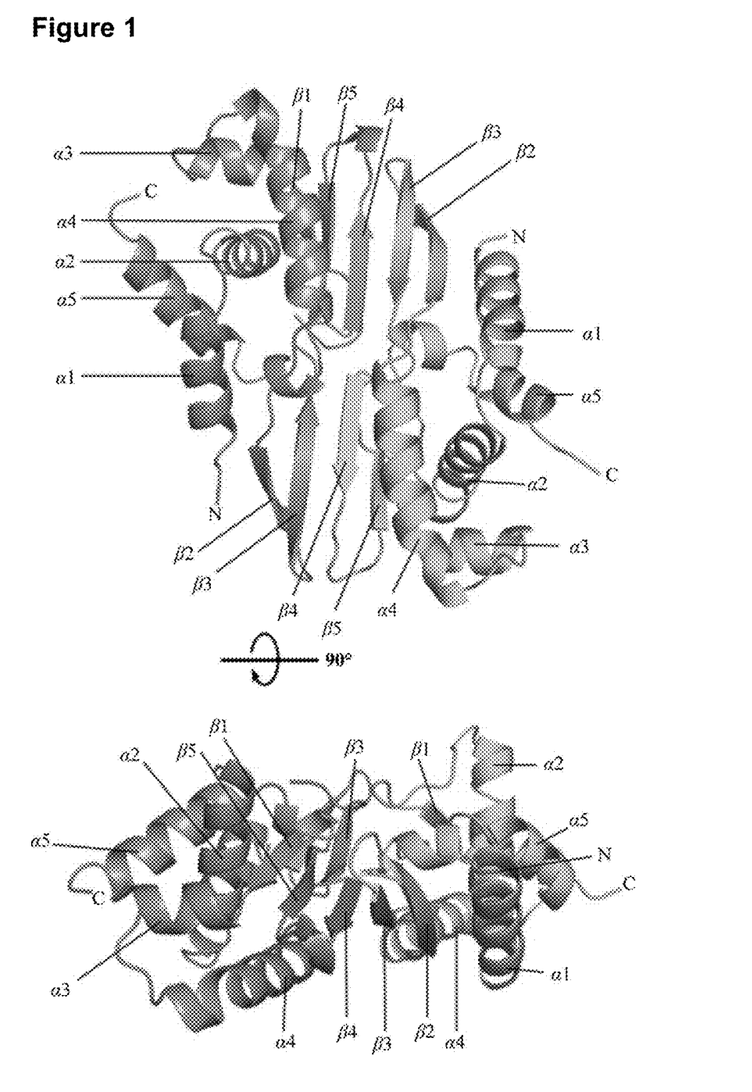
FIG. 1. The X-ray crystal structure of the MSBI1.176 WH1 dimer.

During the experiments resulting in the present invention, the X-ray crystal structure of the MSBI1.176 WH1 domain (residues 2-133) was solved to 1.53 Å resolution (data statistics are given in Table 1). The asymmetric unit consisted of one WH1 dimer, i.e., two protomers (termed A and B). The electron density was well resolved for most of the protein (av. B-factor=29.43 Å$^2$). However, residues 36-39 could not be fitted into the B protomer due to lack of discernible electron density, although the electron density was distinct in the other protomer. The WH1 structure comprised of five α-helixes (α1-α5) and five β-strands (β1-β5) in each protomer (FIG. 1). The A and B protomers were closely related (RMSD=0.37 Å), however, a minor structural shift was observed at the β2-β hairpin, suggesting some flexibility of this region. Importantly, with this improved resolution over previous structures (24-27), water molecules were effectively added to this Rep structure.

The data collection and refinement statistics of the MSBI1.176 WH1 protein structure are summarized in Table 1:

TABLE 1

Data collection and refinement statistics of the MSBI1.176 WH1 protein structure.

| Parameter | Values for S-SAD | Values for S-SAD Native | Values for Native (PDB code 6H24) |
|---|---|---|---|
| Data collection | | | |
| ESRF beamline | ID23-1 | ID23-1 | ID30B |
| Wavelength (Å) | 1.850 | 0.972 | 0.979 |
| No. of crystals | 7 | 1 | 1 |
| Space group | P21 | P21 | P21 |
| Cell dimensions | | | |
| a, b, c (Å) | 104.86 43.96 107.71 | 104.86 43.96 107.71 | 32.38 77.77 47.68 |
| α, β, γ (°) | 90 97.72 90 | 90 97.72 90 | 90 90.66 90 |
| Resolution range (Å) | 19.91-2.30 (2.38-2.30)$^a$ | 19.91-1.58 (1.63-1.58)$^a$ | 40.65-1.53 (1.58-1.53)$^a$ |
| Rmerge (%) | 11.20 (52.00)$^a$ | 4.00 (92.70)$^a$ | 4.09 (68.48)$^a$ |
| I/σI | 33.30 (9.60)$^a$ | 15.80 (1.30)$^a$ | 20.91 (1.98)$^a$ |
| Completeness (%) | 99.90 (98.30)$^a$ | 98.30 (95.3)$^a$ | 99.42 (96.93)$^a$ |
| Redundancy | 84.0 (28.5)$^a$ | 3.7 (3.4)$^a$ | 6.4 (6.1)$^a$ |

TABLE 1-continued

Data collection and refinement statistics of the MSBI1.176 WH1 protein structure.

| Parameter | Values for S-SAD | Values for S-SAD Native | Values for Native (PDB code 6H24) |
|---|---|---|---|
| Refinement | | | |
| Resolution range (Å) | | | 40.65-1.53 |
| No. of reflections | | | 35692 |
| Rwork/Rfree (%) | | | 18.33/20.74 |
| No. of atoms | | | |
| Protein | | | 2029 |
| Water | | | 152 |
| Average B factors (Å2) | | | |
| Protein | | | 29.43 |
| Water | | | 32.58 |
| RMSD | | | |
| Bond lengths (Å) | | | 0.005 |
| Bond angles (°) | | | 1.080 |

$^a$Values in parentheses are for the highest-resolution shell.

Figure 2:
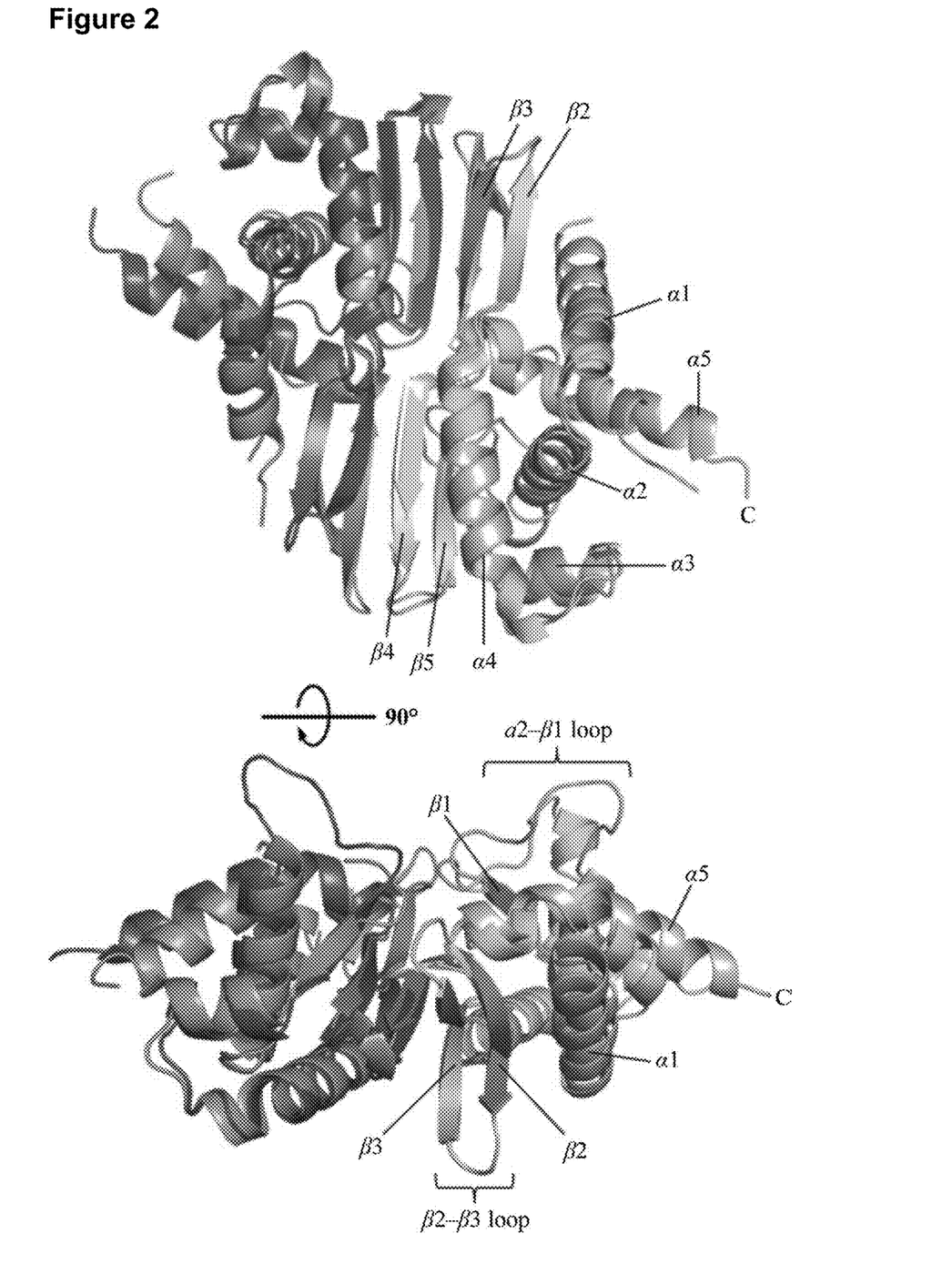
FIG. 2. Structural comparison to closely matching prokaryote RepA WH1.
Figure 3:
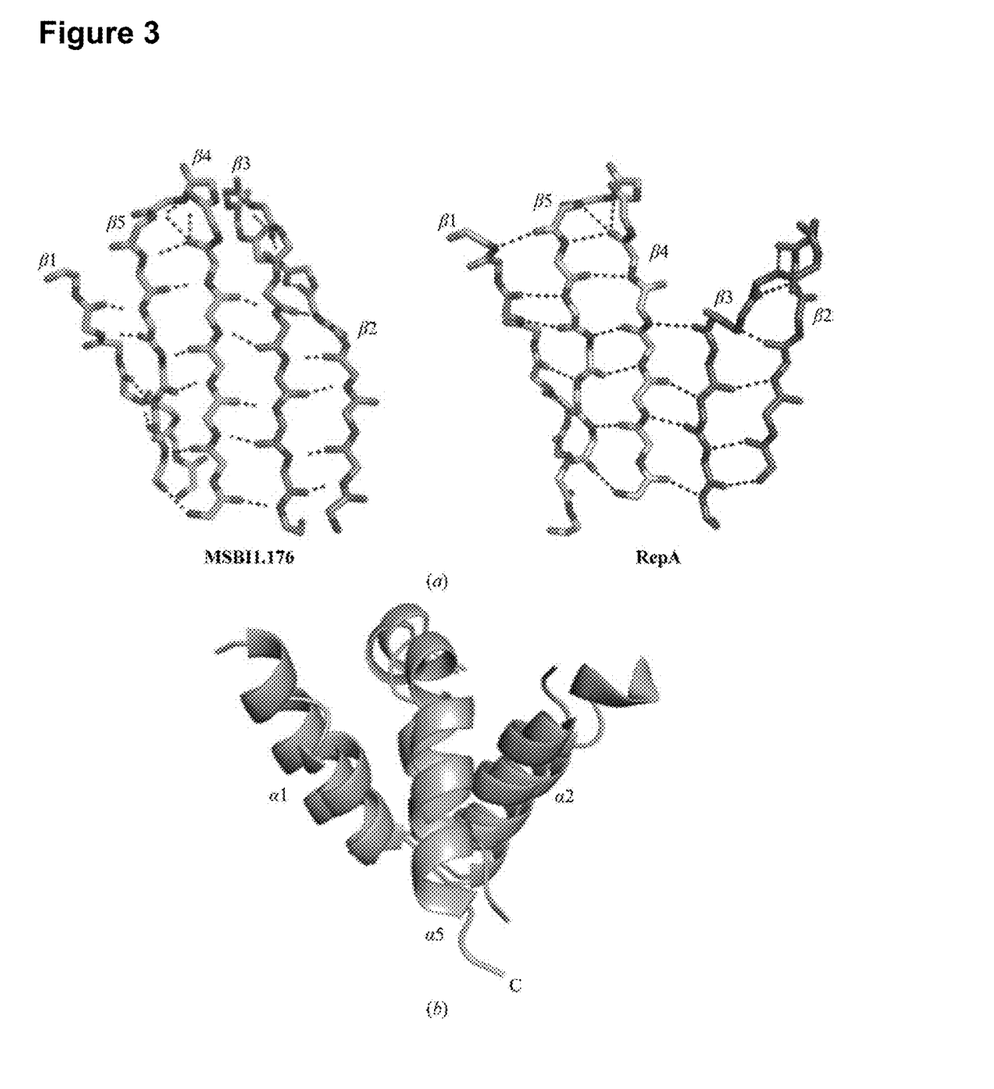
FIG. 3. MSBI1.176 WH1 structural similarities of MSBI1.176 WH1.

A database search for closely related structures and sequences revealed that MSBI1.176 WH1 had an exceptionally low amino acid identity of 28% and 17% amino acid identity with *Pseudomonas syringae* RepA WH1 (dRepA, PDB ID 1HKQ) and *Escherichia coli* RepE fused WH1-2 (RepE54, 1REP), respectively (24, 25). Similar to the dRepA, the MSBI1.176 WH1 was also folded as the replication-inert dimer, while RepE54 (WH1-2 construct) was crystallized in the monomeric initiator form. Superposition of MSBI1.176 WH1 and dRepA WH1 showed that these two domains were structurally similar (RMSD=1.20 Å), both having the typical five α-helix and five β-strands (FIG. 2). A number of structural similarities and differences were observed between these two Reps. The MSBI1.176 and dRepA dimeric interfaces, which involved five β-strands (β1-β5-β4-β3-β2), were held with a similar number of main-chain binding interactions, although not at identical residues (FIG. 3A). This result suggested that the dimeric interface feature was likely functional related among the diverse Rep isolates. The inventors observed that water molecules bound at this dimeric interface (FIG. 3B). However, how these water molecules stabilize the dimeric interface and/or are displaced after binding DNA and changing conformation is not yet known.

The inventors also observed that the MSBI1.176 WH1 region that comprised of α1-α2-α5 was similar in orientation as the dRepA, having the typical α1-α2 bend thereby making a V-shaped structure (FIG. 3C). This region of dRepA forming the linker to WH2, also contained the hydrophobic heptad pocket, which typically contained a number of leucine residues (e.g., dRepA: Leu12, Leu19, and Leu26; RepE: Leu24, Leu31, and Leu39). The MSBI1.176 WH1 hydrophobic pocket also comprised or consisted of three leucine residues, i.e., Leu11, Leu18 and/or Ile25, which were similarly positioned as within dRepA. Not surprising, water molecules were absent in the MSBI1.176 WH1 hydrophobic pocket (FIG. 3B).

Figure 4:
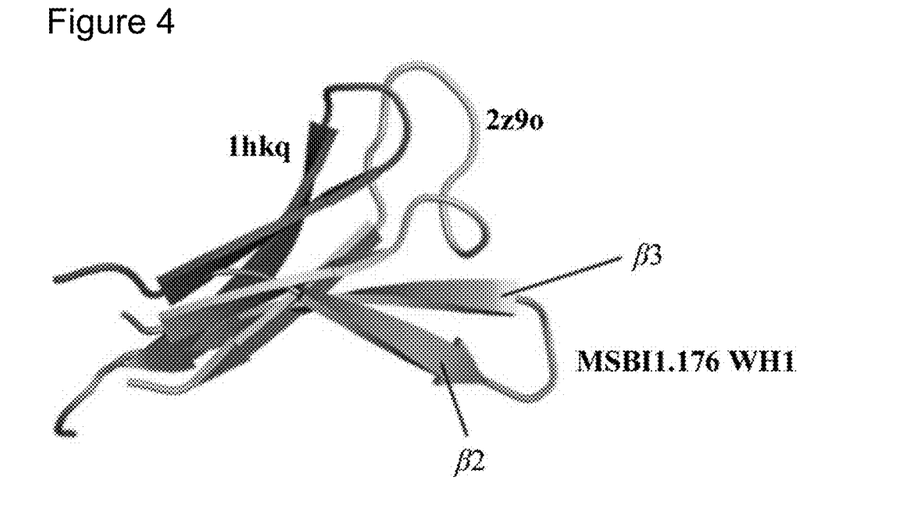
FIG. 4. Superimposition of the MSBI1.176 WH1 β2-β3 hairpin onto prokaryotic Rep proteins with PDB codes 1hkq (RepA) and 2z9o (RepE).
Figure 5:
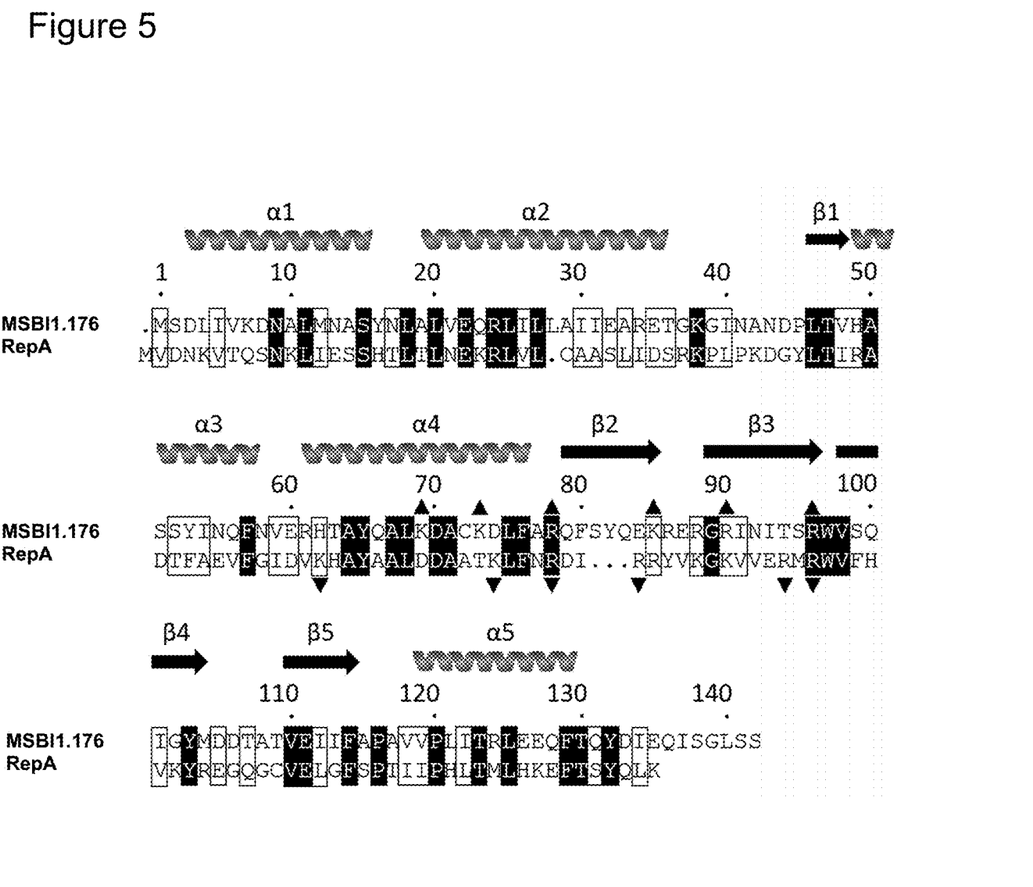
FIG. 5. Amino Acid Sequence Alignment.

In general, many MSBI1.176 WH1 structural features were conserved to other known dimeric Rep structures (24-27). However, loop movements and different α-helix and β-strands have been observed among the different structures. In the case of the MSBI1.176, the β2-β3-hairpin shifted approximately 23 Å when compared to the dRepA β2-β3-hairpin (FIG. 4). In the case of the RepE54, this equivalent β2-β3-hairpin (residues 97-110) was not added to the structure, since the electron density was lacking (20, 24). It was suggested that the RepE54 β2-β3-hairpin was flexible and this flexibility might function by destabilizing the antiparallel β2-β3-hairpin and blocking dimerization (20, 24). However, the MSBI1.176 WH1 β2-β3-hairpin was clearly held with direct main-chain interactions, not unlike the dRepA structure (FIG. 3A). Moreover, we perceived that water-mediated interactions at this dimeric interface might also add further stability to this hairpin (FIG. 3B).

Previous modeling analysis of the dRepA domain indicated that six basic residues on the α2, β2, β3, and adjacent loops (dRepA numbering: Lys74, Arg81, Arg91, Arg93, Lys62, and Arg78) might follow a minor groove of a DNA backbone (24). In the MSBI1.176 WH1 structure, six basic residues were also found in this region. These are considered to represent the DNA-interacting site comprising or consisting of Lys69, Lys73 (located on α2), Lys85 (β2), Arg90 (β3), Arg78, and/or Arg96 (on adjacent loops). In the DNA-interacting site preferably positively charged amino acids are accumulated to make an electrostatic interaction with the negative charges of the DNA. Although, the electron density for MSBI1.176 WH1 Lys73$^{A/B\ chains}$, Lys85$^{A/B\ chains}$ and Arg90$^{A\ chain}$ side-chains were weak, two of these residues (Arg78 and Arg96) were at equivalent dRepA positions and were suggested to interact with a DNA molecule (24). The function of the MSBI1.176 WH1 β2-β3 sheet orientation is not obvious, although the MSBI1 WH1 had a three amino acid insertion in the β2-strand that extended the sheet. Presumably, this insertion elegantly shifted MSBI1.176 WH1 Lys85 (β2) and Arg90 (β3) on the β2-β3 sheet when compared to equivalent dRepA residues Arg81 and Arg91. Seen in another way, MSBI1.176 β2-β3 sheet was rather flattered, whereas the dRepA β2-β3 hairpin was hooking in an opposite direction (FIG. 2).

Elucidation of the MSBI1.176 WH1 structure represents a crucial step forward in better understanding how structural features might change among Rep proteins among this diverse group of BMMF DNAs. The finding that this MSBI1.176 WH1 protein isolated from a patient with multiple sclerosis was closely similar to a prokaryote Rep structure has important consequences. Altogether, this new structural information supports the development and design of new drug targets that can inhibit the oligomeric nature of Reps. According to the present invention a Rep WH1 domain encoded on a BMMF (MSBI1.176) isolated from a multiple sclerosis human brain sample was determined to 1.53 Å resolution using X-ray crystallography. The overall structure of the MSBI1.176 WH1 was remarkably similar to other Rep structures, despite having a low (28%) amino acid identity. The MSBI1.176 WH1 contained elements common to other Reps, including five α-helix, five β-strands, and a hydrophobic pocket. Interestingly, the MSBI1.176 WH1 β2-43 hairpin shifted approximately 23 Å when compared to other Reps. This region is known to interact with DNA and an amino acid insertion in the MSBI1.176 WH1 hairpin shifted positively charged DNA-binding residues further along the β2-β3 sheet. The data of the present invention also show that water molecules additionally stabilize α-helix and β-strands in the protein. Altogether, these new findings support that the MSBI1.176 Rep might have comparable roles and functions as other known Reps from different origins.

Further, the present invention enables to establish methods for identifying inhibitors MSBI1.176 as well as methods for preparing crystal forms of MSBI1.176 Rep protein and their crystal structure information. The data enable rational drug design based on the use of such structural data.

The present invention provides also the possibility to identify and/or design inhibitors of MSBI 1.176 Rep protein and relates to the crystal form of, the crystal structure information obtained from the crystal form, methods of preparing such a crystal form, its use for the identification and/or design of inhibitors of MSBI 1.176 Rep protein activity and the diagnostic and/or pharmaceutical use of those inhibitors of MSBI 1.176 Rep protein identified by these methods.

The terms "crystal form" or "crystal structure" (which are used interchangeably) refer to a crystal form of the MSBI1.176 Rep protein with or without detergents and/or nucleic acids (in particular DNA) bound to the MSBI1.176 Rep protein.

The term "unit cell" as used herein refers to the smallest repeating unit that can generate a crystal with only translation operations. The unit cell is the smallest unit of volume that contains all of the structural and symmetry information of a crystal and that by translation can reproduce a pattern in all of space. Structural information is thereby the pattern (atoms) plus all surrounding space and symmetry information means mirrors, glides, axes, and inversion centers. The translation refers to motion along a cell edge the length of the cell edge. An asymmetric unit is the smallest unit that can be rotated and translated to generate one unit cell using only the symmetry operators allowed by the crystallographic symmetry. The asymmetric unit may be one molecule or one subunit of a multimeric protein, but it can also be more than one. Hence the asymmetric unit is the smallest unit of volume that contains all of the structural information and that by application of the symmetry operations can reproduce the unit cell. The shape of the unit cell is constrained by the collection of symmetry elements which make-up the group. For space groups, seven lattice types are possible: triclinic, monoclinic, orthorhombic, tetragonal, hexagonal, rhombic and cubic. In crystallography, space groups are also called the crystallographic or Fedorov groups. The edges of the unit cell define a set of unit vector axes a, b, and c, with the unit cell dimensions as their respective length a, b, and c. These vectors need not be at right angles, and the angles between the axes are denoted α as between the bc-axes, β between the ac-axes, and γ between the ab-axes. The different shapes arise depending on restrictions placed on the lengths of the three edges (a, b, and c) and the values of the three angles (α, β, and γ).

In another preferred embodiment of the present invention the crystal form of MSBI 1.176 Rep protein contains or further contains a hydrophobic pocket, wherein the hydrophobic pocket contains the amino acids Leu11, Leu18 and Ile25.

A potential inhibitor of MSBI 1.176 Rep protein could bind to the DNA-interacting site in order to decrease the activity of the Rep protein. Thus, a method for designing, identifying and/or optimizing compounds which might have the ability to bind to MSBI1.176 Rep protein could be based on the crystal structure coordinates.

A potential inhibitor of MSBI1.176 Rep protein could bind to a Rep oligomerization interface modulating structure-based function and protein activity/localization/stability/modification.

A potential inhibitor of MSBI1.176 Rep protein could bind to yet unknown protein interaction surfaces modulating structure-based function and protein activity/localization/stability/modification.

A potential inhibitor of MSBI1.176 Rep protein could bind to structurally-related prokaryotic Rep (e.g. from *Acinetobacter baumannii* species) to decrease the activity of such Rep proteins from different origin based on sterical hindrance of DNA-binding, oligomerization and/or addition protein interaction interfaces.

The crystal forms of MSBI1.176 Rep protein as disclosed herein can be obtained by the following crystallization method. Thus the present invention relates to a method for crystallizing MSBI1.176 Rep protein comprising the steps:

(a) preparing a solution of recombinant prepared MSBI1.176 WH1 domain in a crystallization reagent, preferably containing at least one inorganic salt and at least one precipitation agent;
(b) crystallizing said MSBI1.176 WH1 domain by vapor diffusion.

The at least one inorganic salt is used in an amount of between 0.01 mM and 2 M, preferably 0.1 mM and 1 M, more preferably between 0.1 M and 0.5 M, more preferably about 0.2 M. In case more than one inorganic salt is used, the afore-mentioned concentration refers to the concentration of all inorganic salts together and not to the concentration of each single salt used in the mixture of inorganic salts.

Preferably, inorganic salts are selected from the group comprising or consisting of ammonium chloride, ammonium sulfate, ammonium acetate, ammonium fluoride, ammonium bromide, ammonium iodide, ammonium nitride, calcium chloride, calcium acetate, magnesium acetate, magnesium formate, magnesium nitrate, potassium acetate, potassium bromide, potassium fluoride, potassium chloride, potassium iodide, potassium nitrate, sodium acetate, sodium hydroxide, sodium bromide, sodium fluoride, sodium iodide, sodium nitrate, sodium sulfate, sodium chloride, zinc chloride, zinc sulfate, zinc acetate. A preferred inorganic salt is magnesium acetate.

In theory, the at least one precipitating agent competes with the protein solutes for water, thus leading to supersaturation of the proteins. Crystals can normally only grow from supersaturated states, and thus they can grow from precipitates. Salts, polymers, and organic solvents are suitable precipitating agents which are used in an amount between 5% by weight and 50% by weight, preferably between 10% by weight and 40% by weight, and more preferably between 15% by weight and 35%, and most preferably between 20% by weight and 30% by weight of the precipitating agent or the mixture of precipitating agents in regard to the total weight of the buffered precipitant solution.

The precipitating agent used in the buffered precipitant solution of step (b) may preferably be selected from the group consisting of or comprising: 2-methyl-2,4 pentanediol, glycerol, polyethylene glycol (PEG), pentaerythritol propoxylate, pentaerythritol ethoxylate, sodium polyacrylate, hexandiol, isopropanol, ethanol, tert-butanol, dioxane, ethylene imine polymer, ethylene glycol, propanediol, polyacrylic acid, polyvinylpyrrolidone, 2-ethoxyethanol, or mixtures thereof. Most preferred as the precipitant is PEG, preferably having molecular weights ranging from PEG 200 to PEG 20,000, more preferably having molecular weights range from PEG 1,000 to PEG 18,000, yet more preferably having molecular weights range from PEG 3,000 to PEG 15,000. PEG is a very preferred precipitating agent which is preferably used in an amount of 20-30% by weight of the buffered precipitant solution.

In a most preferred embodiment the crystallization buffer contains 0.2 M magnesium acetate and 20% PEG3350.

In a preferred embodiment the hanging-drop or the sitting-drop methods are used for crystallization. "The hanging drop vapor diffusion" technique is the most popular method for the crystallization of macromolecules. The principle of vapor diffusion is straightforward. A drop composed of a mixture of sample and crystallization reagent is placed in vapor equilibration with a liquid reservoir of reagent. Typically the drop contains a lower reagent concentration than the reservoir. To achieve equilibrium, water vapor leaves the drop and eventually ends up in the reservoir. As water leaves the drop, the sample undergoes an increase in direction to super-saturation. Both the sample and reagent increase in concentration as water leaves the drop for the reservoir. Equilibration is reached when the reagent concentration in the drop is approximately the same as that in the reservoir.

Further important aspects of the invention are related to the use of the crystal forms of MSBI1.176 Rep protein for an in-silico prediction model for the identification, optimization and/or design of inhibitors of MSBI1.176 Rep protein. Knowing the exact positions of the atoms of the amino acids in the DNA-interacting site provides the possibility to design suitable inhibitors, identify suitable inhibitors e.g. from a compound library or optimize a known suitable inhibitor by increasing the inhibitory potential. Design, identification and optimization of suitable inhibitors can be performed with standard computer-based methods and software programs well known in the art. A variety of commercially available software programs are available for conducting the analysis and comparison of data in the computer-based system. One skilled in the art will readily recognize which of the available algorithms or implementing software packages for conducting computer analyses can be utilized or adapted for use in the computer-based system. A target structural motif or target motif refers to any rationally selected sequence or combination of sequences in which the sequence(s) are chosen based on a three-dimensional configuration or electron density map which is formed upon the folding of the target motif. There are a variety of target motifs known in the art. A variety of structural formats for the input and output means can be used to input and output the information in the computer-based systems of the present invention. A variety of comparing means can be used to compare a target sequence or target motif with the data storage means to identify structural motifs or interpret electron density maps derived in part from the atomic coordinate/x-ray diffraction data. One skilled in the art can readily recognize any one of the publicly available computer modeling programs that can be used. Suitable software that can be used to view, analyze, design, and/or model a protein comprise Alchemy™, LabVision™, Sybyl™, Molcadd™, Leapfrog™, Matchmaker20™, Genefold™ and Sitel™ (available from Tripos Inc., St. Louis, Mo.); Quanta™, MacroModel™ and GRASP™, Univision™, Chem 3D™ and Protein Expert™.

Thus in a further aspect the present invention is related to methods for designing, identifying and optimizing inhibitors of MSBI1.176 Rep protein by applying the crystal form and the related structure coordinates of the crystal form or at least of one of the DNA-interacting sites in order to design, identify or optimize inhibitors by means of computer based methods or software programs.

The atomic coordinate/x-ray diffraction data may be used to create a physical model which can then be used to design molecular models of compounds that should have the ability or property to inhibit and/or interact with the determined DNA-interacting sites or other structural or functional domains or subdomains such as the hydrophobic pocket and/or the pocket neighboring the DNA-interacting site. Alternatively, the atomic coordinate/x-ray diffraction data of the complex may be represented as atomic model output data on computer readable media which can be used in a computer modeling system to calculate different molecules expected to inhibit and/or interact with the determined sites, or other structural or functional domains or subdomains. For example, computer analysis of the data allows one to calculate the three-dimensional interaction of the MSBI1.176 Rep protein and the compound to confirm that the compound binds to, or changes the conformation of, particular domain(s) or subdomain(s). Compounds identified from the analysis of the physical or computer model can then be synthesized and tested for biological activity with an appropriate assay.

In case an inhibitor is identified from a compound library or in case a known inhibitor is optimized by theoretical chemical modifications, testing of the actual compound is desired in order to verify the inhibitory effect and to continue the optimization process. Thus, preferably the above method for identifying and/or optimizing a compound further comprising the steps of (a) obtaining the identified or optimized compound; and
(b) contacting the identified or optimized compound with MSBI1.176 Rep protein in order to determine the inhibitory effect on MSBI1.176 Rep protein.

It is not necessary to use all the structure coordinates as listed in Table 1. Thus only the structure coordinates of the hydrophobic pocket and/or the DNA-interacting site could be used.

In this application, a Rep WH1 domain encoded on a BMMF (MSBI1.176) isolated from a multiple sclerosis human brain sample was determined to 1.53 Å resolution using X-ray crystallography. The overall structure of the MSBI1.176 WH1 was remarkably similar to other Rep structures, despite having a low (28%) amino acid identity. The MSBI1.176 WH1 contained elements common to other Reps, including five α-helix, five β-strands, and a hydrophobic pocket. These new findings suggest that the MSBI1.176 Rep might have comparable roles and functions as other known Reps from different origins. Reps are important for replication of plasmids or autarkic episomal nucleic acids in different hosts. Hence, it has been considered that such proteins and Rep-encoding DNAs might be linked with diseases. Thus, careful structural and functional characterization of Reps is needed. The Rep described in this study is encoded by human bioactive bovine meat and milk factor MSBI1.176, which was isolated from a patient with multiple sclerosis. Specific serum antibodies were found in a set of healthy human blood bank donors pointing at a general human exposure towards such agents. The discovery that this MSBI1.176-encoded Rep WH1 protein was closely similar to a prokaryote Rep structure might have important consequences and point towards a possible disease-correlated adaptation of these agents towards humans. This new structural information might aid in the development and design of therapeutic/preventive drugs that can inhibit these Reps of diverse origin.

The following abbreviations are used for the common and modified amino acids referred to herein.

Amino Acids
Ala Alanine
Arg Arginine
Asn Asparagine
Asp Aspartic acid (Aspartate)
Cys Cysteine
Gln Glutamine
Glu Glutamic acid (Glutamate)
Gly Glycine
His Histidine
Ile Isoleucine
Leu Leucine
Lys Lysine
Met Methionine
Phe Phenylalanine
Pro Proline
Ser Serine
Thr Threonine
Trp Tryptophan
Tyr Tyrosine
Val Valine

DESCRIPTION OF THE FIGURES

The MSBI1.176 WH1 protomers are colored cyan for chain A and orange for chain B. One protomer comprises five α-helices (α1-α5) and five β-strands (β1-β5). The dimeric interface involves two strands (β4-β3).

MSBI1.176 WH1 and RepA WH1 have 28% amino-acid identity. Superposition with RepA (gray) showed that these two WH1 dimers are highly similar, with an r.m.s.d. of 1.20 Å. Structural differences in extended loops were observed, noticeably the loops connecting α2 and β1 as well as β2 and β3.

(A) The five β-sheets (β1-β5-β4-β3-β2) showing the main-chain interactions in MSBI1.176 WH1 (cyan and orange) and RepAWH1 (gray). The β-strands were held by numerous main-chain hydrogen bonds (dashed lines), similar to RepA, including the dimeric interface (β4-β3).

(B) The region containing α1-α2-α5 was similar in orientation to that in RepA. This region produced a V-shaped structure and α5 is the linker region to the WH2 domain. The hydrophobic pocket also contained three leucine residues, i.e. Leu11, Leu18 and Ile25, which were similarly positioned in RepA (data not shown).

The MSBI1.176 WH1 β2-3 hairpin shifted approximately 23 Å when compared with the equivalent RepA hairpin. The MSBI1.176 WH1 β2-3 hairpin was held by direct main-chain interactions (FIG. 3a) as well as water-mediated interactions. Note the different β2-3 hairpin twists between the MSBI1.176 and RepA WH1 structures in FIG. 3(A). The RepE β2-β3 hairpin was positioned between these two WH1 β2-β3 hairpins.

The amino acid sequence alignment of MSBI1.176 (LK931491.1), amino acids 1-142 of SEQ ID NO: 1, and RepA (PDB ID 1HKQ), SEQ ID NO: 2 was generated using ClustalW (Genetyx). Secondary structural elements are shown and confirmed using the crystal structure. Identical and homologous residues are highlighted in filled background or boxes, respectively. Presumably, a DNA molecule would interact along the dimeric interface and with possibly six basic residues in this region, i.e., Lys69 (α4), Lys73 (α4), Arg78, Lys85 (β2), Arg90 (β3), and Arg96. The basic amino acid residues of RepA that were suggested to participate in DNA interaction are marked with upside-down triangles (▽) and the equivalent for MSBI1.176 WH1 were marked with triangles (▲).

The following examples are included to demonstrate preferred embodiments of the invention. It should be appreciated by those of skill in the art that the techniques disclosed in the following examples represent techniques discovered by the inventor to function well in the practice of the invention, and thus can be considered to constitute preferred modes for its practice. Modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention.

EXAMPLES

Example 1: Method of Obtaining Crystals of MSBI1 WH1

The MSBI1.176 DNA (LK931491.1) was isolated from a brain sample of a patient with multiple sclerosis (11). The MSBI1 WH1 domain (residues 1-135) was expressed in *E. coli* and purified as previously described for human norovirus protruding domains (29). Briefly, the codon optimized WH1 was cloned in a modified expression vector pMal-c2X (Geneart) and transformed into BL21 cells for protein expression. Transformed cells were grown in LB medium supplemented with 100 µg/ml ampicillin for 4 hours at 37° C. Expression was induced with IPTG (0.75 mM) at an $OD_{600}$ of 0.7 for 18 h at 22° C. Cells were harvested by centrifugation at 6000 rpm for 15 min and disrupted by sonication on ice. His-tagged fusion-MBSI1 protein was initially purified from a Ni column (Qiagen), dialyzed in a gel filtration buffer (GFB: 25 mM Tris-HCl and 300 mM NaCl) with 10 mM imidazole and digested with HRV-3C protease (Novagen) overnight at 4° C. The cleaved MSBI1 WH1 was then applied on the Ni column again to separate and collect the cleaved protein, and dialyzed in GFB overnight at 4° C. The MSBI1 WH1 protein was further purified by size exclusion chromatography, concentrated to 5 mg/ml and stored in GFB at 4° C. Crystals of MSBI1 WH1 were grown using hanging-drop vapor diffusion method at 18° C. for ~6-10 days in a 1:1 mixture of protein sample and mother liquor (0.2 M magnesium acetate and 20% PEG3350). Prior to data collection, MSBI1 WH1 crystals were transferred to a cryoprotectant containing the mother liquor with 40% PEG3350, followed by flash freezing in liquid nitrogen.

Example 2: X-Ray Diffraction

X-ray diffraction data of the MSBI1 WH1 domain were collected on the European Synchrotron Radiation Facility (ESRF) on beamlines ID23-1 and ID30B. For the single-wavelength anomalous diffraction using native sulfurs (S-SAD) experiments, diffraction data from seven crystals were collected at $\lambda=1.850$ Å on beamline ID23-1 equipped with Dectris pixel array detector PILATUS-6M. The X-ray beam size at the sample position was 50 µm and the size of crystals was approximately $70\times7\times200$ µm$^3$. To decrease the radiation damage effects, the helical data collection strategy was applied. One native data set was collected at ID23-1 at $\lambda=0.972$ Å for initial phase extension and a second native data set was collected at ID30B at $\lambda=0.979$ Å for structure refinement. Optimal experimental parameters for data collection were designed using the BEST (30) incorporated into the MxCube software (31) at ESRF. The single native date set was processed with XDS while multiple data sets for S-SAD were processed with XDS and then merged using XSCALE (32).

Several data sets were collected using S-SAD for further processing (33). S-SAD phasing protocol was carried out using the SHELXC/D/E pipeline as implemented in HKL2MAP (34). One thousand trials were carried out for substructure determination in SHELXC. Using a resolution of 2.3 Å and an anomalous signal truncated to 3.1 Å, SHELXD correctly identified all 24 sulfur sites. Four hundred and fifteen residues were built automatically by SHELXE, which resulted in an interpretable map for further processing. Finally ARP-wARP was then used for automated model building based on the first S-SAD native data set collected (35). The structure was refined using the second high resolution native data set in multiple rounds of manual model building in COOT (36) and PHENIX (37). The structure was validated using Molprobity and Procheck. Interactions were analyzed using Accelrys Discovery Studio (Version 4.1), with hydrogen bond distances between 2.4-3.5 Å. Figures and protein contact potentials were generated using PyMOL. Atomic coordinates and structure factors have been deposited in the Protein Data Bank (PDB) with the accession code of 6H24.

Example 3: Modeling of DNA Binding

Previous modeling analysis of the RepA domain indicated that six basic residues on the α2, β2, β3, and adjacent loops (RepA numbering: Lys74, Arg81, Arg91, Arg93, Lys62, and Arg78) might follow a minor groove of a DNA backbone (24). In the MSBI1.176 WH1 structure, six basic residues were also found in this region, i.e., Lys69, Lys73 (both located on α4), Lys85 (β2), Arg90 (β3), Arg78 and Arg96 (both on adjacent loops). Although, the electron density for MSBI1.176 WH1 Lys73$^{A/B\ chains}$, Lys85$^{A/B\ chains}$ and Arg90$^{A\ chain}$ side-chains were weak, two of these residues (Arg78 and Arg96) were at equivalent RepA positions and were suggested to interact with a DNA molecule (24). The function of the MSBI1.176 WH1 β2-β3 sheet orientation is not obvious, although the MSBI1.176 WH1 had a three amino acid insertion in the β2-strand that extended the sheet. Presumably, this insertion elegantly shifted MSBI1.176 WH1 Lys85 (β2) and Arg90 (β3) on the β2-β3 sheet when compared to equivalent RepA residues Arg81 and Arg91. Seen in another way, MSBI1.176 β2-β3 sheet was rather flattered, whereas the RepA β2-β3 hairpin was hooking in an opposite direction.

REFERENCES

1. Chan D S, et al. (2011) Red and processed meat and colorectal cancer incidence: meta-analysis of prospective studies. *PloS one* 6(6):e20456.

2. Corpet D E (2011) Red meat and colon cancer should we become vegetarians, or can we make meat safer? *Meat science* 89(3):310-316.
3. Huxley R R, et al. (2009) The impact of dietary and lifestyle risk factors on risk of colorectal cancer: a quantitative overview of the epidemiological evidence. *International journal of cancer* 125(1):171-180.
4. zur Hausen H & de Villiers E M (2015) Dairy cattle serum and milk factors contributing to the risk of colon and breast cancers. *International journal of cancer* 137(4):959-967.
5. Zur Hausen H, Bund T, & de Villiers E M (2017) Infectious Agents in Bovine Red Meat and Milk and Their Potential Role in Cancer and Other Chronic Diseases. *Current topics in microbiology and immunology* 407:83-116.
6. zur Hausen H (2012) Red meat consumption and cancer reasons to suspect involvement of bovine infectious factors in colorectal cancer. *International journal of cancer* 130(11):2475-2483.
7. zur Hausen H (2015) Risk factors: What do breast and CRC cancers and MS have in common? *Nat Rev Clin Oncol* 12(10):569-570.
8. Funk M, et al. (2014) Isolation of protein-associated circular DNA from healthy cattle serum. *Genome announcements* 2(4).
9. Falida K, Eilebrecht S, Gunst K, Zur Hausen H, & de Villiers E M (2017) Isolation of Two Virus-Like Circular DNAs from Commercially Available Milk Samples. *Genome announcements* 5(17).
10. zur Hausen H, Bund T, & de Villiers E-M (In press) Specific Nutritional Infections Early in Life as Risk Factors for Human Colon and Breast Cancers Several Decades Later. *International Journal of Cancer.*
11. Whitley C, et al. (2014) Novel replication-competent circular DNA molecules from healthy cattle serum and milk and multiple sclerosis-affected human brain tissue. *Genome announcements* 2(4).
12. Lamberto I, Gunst K, Muller H, Zur Hausen H, & de Villiers E M (2014) Mycovirus-like DNA virus sequences from cattle serum and human brain and serum samples from multiple sclerosis patients. *Genome announcements* 2(4).
13. Gunst K, Zur Hausen H, & de Villiers E M (2014) Isolation of bacterial plasmid-related replication-associated circular DNA from a serum sample of a multiple sclerosis patient. *Genome announcements* 2(4).
14. Kornberg A, and Baker, T. (1992) DNA Replication. *University Science Books* 2nd Ed.
15. Kline B C (1985) A review of mini-F plasmid maintenance. *Plasmid* 14(1):1-16.
16. Ruiz-Maso J A, et al. (2015) Plasmid Rolling-Circle Replication. *Microbiology spectrum* 3(1):PLAS-0035-2014.
17. Schumacher M A, et al. (2014) Mechanism of staphylococcal multiresistance plasmid replication origin assembly by the RepA protein. *Proceedings of the National Academy of Sciences of the United States of America* 111(25):9121-9126.
18. Molina-Garcia L, Gasset-Rosa F, Alamo M M, de la Espina S M, & Giraldo R (2018) Addressing Intracellular Amyloidosis in Bacteria with RepA-WH1, a Prion-Like Protein. *Methods in molecular biology* 1779:289-312.
19. Giraldo R, et al. (2016) RepA-WH1 prionoid: Clues from bacteria on factors governing phase transitions in amyloidogenesis. *Prion* 10(1):41-49.
20. Giraldo R, Moreno-Diaz de la Espina S, Femandez-Tresguerres M E, & Gasset-Rosa F (2011) RepA-WH1 prionoid: a synthetic amyloid proteinopathy in a minimalist host. *Prion* 5(2):60-64.
21. Manuelidis L (2011) Nuclease resistant circular DNAs copurify with infectivity in scrapie and CJD. *Journal of neurovirology* 17(2):131-145.
22. Yeh Y H, Gunasekharan V, & Manuelidis L (2017) A prokaryotic viral sequence is expressed and conserved in mammalian brain. *Proceedings of the National Academy of Sciences of the United States of America* 114(27):7118-7123.
23. Eilebrecht S, et al. (2018) Expression and replication of virus-like circular DNA in human cells. *Scienific reports* 8(1):2851.
24. Giraldo R, Femandez-Tomero C, Evans P R, Diaz-Orejas R, & Romero A (2003) A conformational switch between transcriptional repression and replication initiation in the RepA dimerization domain. *Nature structural biology* 10(7):565-571.
25. Komori H, et al. (1999) Crystal structure of a prokaryotic replication initiator protein bound to DNA at 2.6 A resolution. *The EMBO journal* 18(17):4597-4607.
26. Nakamura A, Wada C, & Miki K (2007) Structural basis for regulation of bifunctional roles in replication initiator protein. *Proceedings of the National Academy of Sciences of the United States of America* 104(47):18484-18489.
27. Swan M K, Bastia D, & Davies C (2006) Crystal structure of pi initiator protein-iteron complex of plasmid R6K: implications for initiation of plasmid DNA replication. *Proceedings of the National Academy of Sciences of the United States of America* 103(49):18481-18486.
28. Forest K T & Filutowicz M S (2003) Remodeling of replication initiator proteins. *Nature structural biology* 10(7):496-498.
29. Hansman G S, et al. (2011) Crystal structures of GII.10 and GII.12 norovirus protruding domains in complex with histo-blood group antigens reveal details for a potential site of vulnerability. *Journal of virology* 85(13):6687-6701.
30. Bourenkov G P & Popov A N (2010) Optimization of data collection taking radiation damage into account. *Acta crystallographica. Section D, Biological crystallography* 66(Pt 4):409-419.
31. Gabadinho J, et al. (2010) MxCuBE: a synchrotron beamline control environment customized for macromolecular crystallography experiments. *Journal of synchrotron radiation* 17(5):700-707.
32. Kabsch W (2010) XDS. *Acta Cryst.* D 66:125-132.
33. Liu Q, et al. (2012) Structures from anomalous diffraction of native biological macromolecules. *Science* 336 (6084):1033-1037.
34. Sheldrick G M (2010) Experimental phasing with SHELXC/D/E: combining chain tracing with density modification. *Acta crystallographica. Section D, Biological crystallography* 66(Pt 4):479-485.
35. Langer G, Cohen S X, Lamzin V S, & Perrakis A (2008) Automated macromolecular model building for X-ray crystallography using ARP/wARP version 7. *Nature protocols* 3(7):1171-1179.
36. Emsley P L B, Scott W G, Cowtan K. (2010) Features and development of Coot. *Acta Crystallographica Section D: Biological Crystallography.* 66(4):486-501.
37. Adams P D, et al. (2010) PHENIX: a comprehensive Python-based system for macromolecular structure solution. *Acta Crystallographica Section D* 66(2):213-221.

The invention claimed is:

1. A crystal form of MSBI1.176 Rep protein having the amino acid sequence of SEQ ID NO: 1, characterized as having (a) a space group of P21 and (b) unit cell dimensions of a=32.38 Å±1-2 Å, b=77.77 Å±1-2 Å and c=47.68 Å±1-2 Å, α=90°, β=90.66° and γ=90°.

2. The crystal form of MSBI1.176 Rep protein of claim 1 containing a hydrophobic pocket comprising Leu11, Leu18 and/or Ile25.

3. The crystal form of MSBI1.176 Rep protein of claim 1 containing a DNA interacting site comprising residues Lys69, Lys73, Lys85, Arg90, Arg78 and/or Arg96.

4. A method for producing the crystal form of MSBI1.176 Rep protein of claim 1, said method comprising the steps of:
(a) preparing a solution of recombinantly prepared MSBI1.176 Rep protein, in a crystallization reagent,
(b) crystallizing said MSBI1.176 Rep protein by vapor diffusion.

5. The method of claim 4, wherein the crystallization reagent contains 0.2 M magnesium acetate and 20% PEG3350.

6. The method of claim 4, wherein the vapor diffusion is hanging-drop vapor diffusion method.

* * * * *